United States Patent [19]

Hong

[11] Patent Number: 4,702,235
[45] Date of Patent: Oct. 27, 1987

[54] THERAPEUTIC INFLATABLE LUMBAR BRACE HAVING A HEATER

[76] Inventor: James K. Hong, 13704 Osborne St., Arleta, Calif. 91331

[21] Appl. No.: 864,834

[22] Filed: May 17, 1986

[51] Int. Cl.$^4$ ............................ A61F 5/02; A61F 7/08
[52] U.S. Cl. ...................................... 128/78; 128/68.1; 128/DIG. 20; 128/402; 128/384
[58] Field of Search ................ 128/68.1, 78, DIG. 20, 128/384, 24.1, 399, 402

[56] References Cited

U.S. PATENT DOCUMENTS

| | | | |
|---|---|---|---|
| 1,603,001 | 10/1926 | Carter | 128/402 |
| 1,646,590 | 10/1927 | Mildenberg | 128/78 |
| 3,548,819 | 12/1970 | Davis et al. | 128/402 |
| 3,561,435 | 2/1971 | Nicholson | 128/402 |
| 3,687,143 | 8/1972 | Schneeberger et al. | 128/402 |
| 3,716,049 | 2/1973 | Kaplan | 128/DIG. 20 |
| 3,974,827 | 8/1976 | Bodeen | 128/DIG. 20 |
| 4,042,803 | 8/1977 | Bickford | 128/384 |
| 4,201,218 | 5/1980 | Feldman et al. | 128/402 |
| 4,279,255 | 7/1981 | Hoffman | 128/399 |
| 4,597,386 | 7/1986 | Goldstein | 128/78 |

FOREIGN PATENT DOCUMENTS

| | | | |
|---|---|---|---|
| 2948059 | 7/1981 | Fed. Rep. of Germany | 128/402 |
| 689674 | 10/1979 | U.S.S.R. | 128/402 |

Primary Examiner—Edgar S. Burr
Assistant Examiner—Tonya Lamb
Attorney, Agent, or Firm—Albert O. Cota

[57] ABSTRACT

The object of the invention is to provide an ambulatory therapeutic brace that substantially supports the lumbar or stomach area with a pneumatically cushioned and heated air chamber (24). A belt (20) surrounds the waist and contains an air chamber (24) on the back inner surface. A heater (26) is embedded integrally with the chamber and is controlled in intensity by a switch (38) attached to the belt or is integral with a buckle (22). The chamber may be inflated by a manual bulb (28), a compressed air source, or an integral electrically operated pump (46).

1 Claim, 7 Drawing Figures

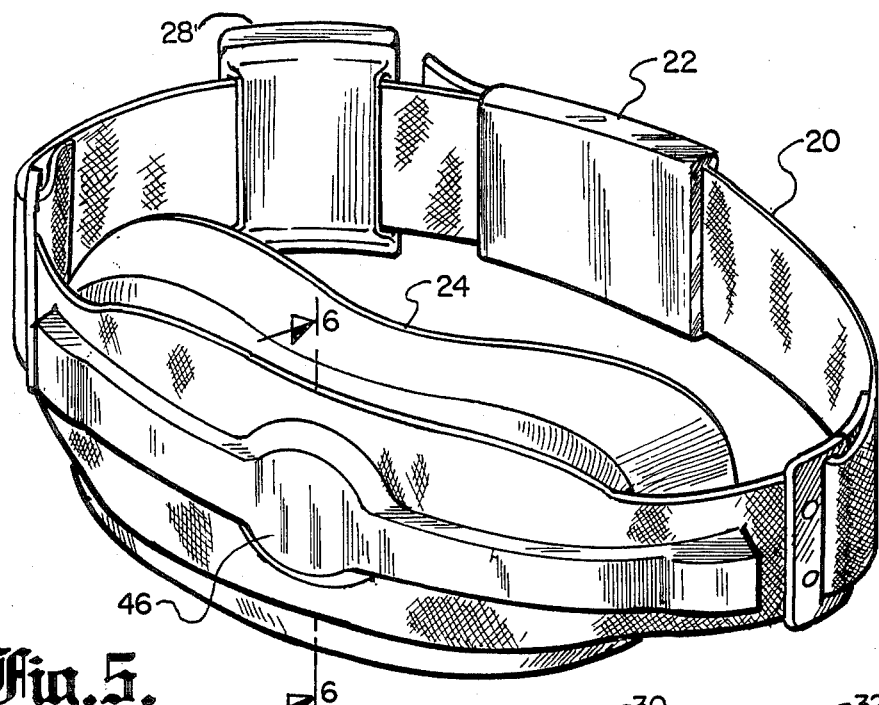
Fig.5.
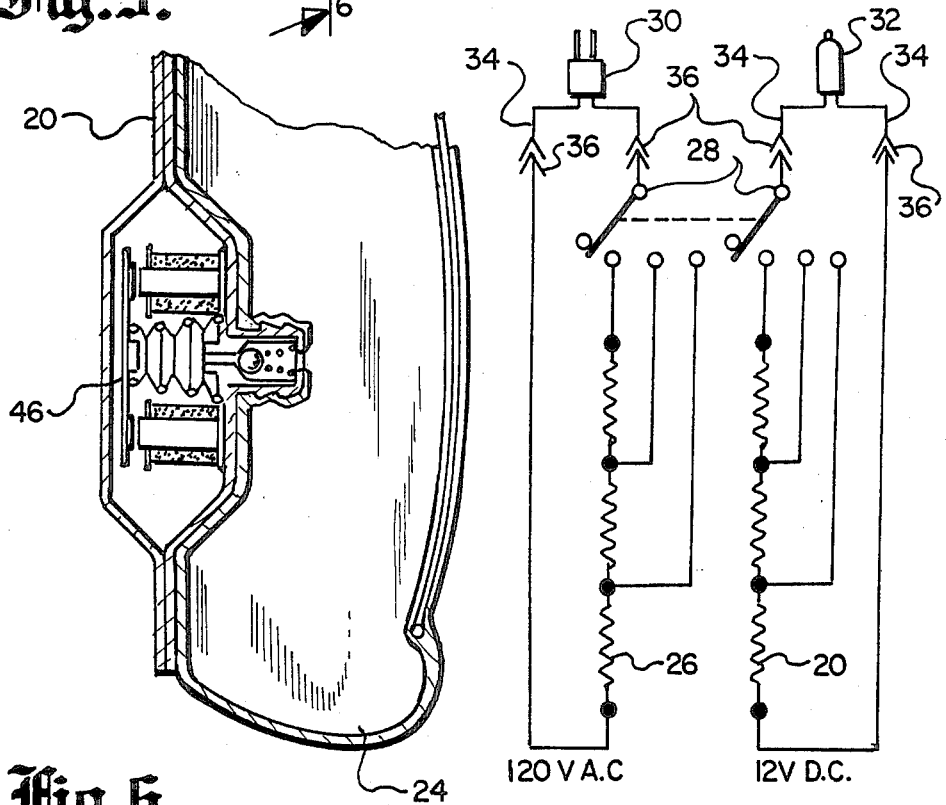
Fig.6.
Fig.7.

THERAPEUTIC INFLATABLE LUMBAR BRACE HAVING A HEATER

TECHNICAL FIELD

The present invention relates to ambulatory brace for the lumbar region of a person's back in general, and more specifically to a pneumatically contoured, electrically heated physiotherapeutic brace.

BACKGROUND ART

Previously, many types of devices have been developed to provide an effective means for relieving low back pain in the lumbar area. Many cushions have been in use that are contoured for not only the lumbar arch, but the sacrum and dorsal regions. Others provide pneumatic inserts that pressurize the area to a desired level of curvature and resiliency for the seat occupant. Others have added heat to cushions and supports. Prior art is replete with rigid and inflatable backs for chairs and automobile seats, also attachable heat bands and lumbosacral corsets have been in wide use.

A search of the prior art did not disclose any patents that read directly on the claims of the instant invention, however, the following U.S. patents were considered related:

| U.S. Pat. No. | Inventor | Issue Date |
| --- | --- | --- |
| 4,497,517 | Gmeiner et al | Feb. 5, 1985 |
| 4,444,430 | Yoshida et al | Apr. 24, 1984 |
| 4,335,725 | Geidmacher | June 22, 1982 |
| 4,279,255 | Hoffman | July 21, 1981 |
| 4,273,989 | Hinton et al | June 16, 1981 |
| 4,042,803 | Bickford | Aug. 16, 1977 |

Gmeiner et al teach a seat cushion for an automobile that contains individually inflatable chambers to support the spinal column of the user of the seat. The chambers are inflated to different hardnesses and are located in specific back areas.

Yoshida et al basically teach the same approach for automobile seating. The inflation, however, is controlled by a manual lever and rubber bag pump, both concealed within the seat. The purpose of this device is to eliminate driver fatigue by applying pressure to the lumbar area and causing that portion of the seat to protrude.

Geidmacher utilizes a cushion that selectively heats and supports portions of a persons back while in a car utilizing the direct current electrical power through the cigarette lighter socket. The cushion has arcuate surfaces with a tapered contour conforming to the users lower back area.

Hoffman applies heat to one's body with a portable heating device with a flexible heating unit attached to a body part raising the skin temperature in the selected area. The heater uses electrical resistance heating elements that are connected through wires to a battery pack using rechargeable lead-acid batteries. A printed circuit board covers the batteries and contains the necessary electrical components operatively connected to the board. The heating elements are embedded in a silicone rubber sheath that is attached directly to the persons skin using hook and loop tape for attachment.

For background purposes and as indicative of the art to which the invention relates reference may be made to the remaining cited patents issued to Hinton et al and Bickford.

DISCLOSURE OF THE INVENTION

Previously, cushions or low back supports are formed either with a rigid member located on the extreme back and covered with resilient material or made entirely of the same substance. The problem that exists is that the cushion is made to fit only the average user and has no allowance for a person's broadness of the lumbar area or shape of the lordotic curve. An orthopedic device, in order to be comfortable and supply the needed support, must conform in every detail to the users back or unnecessary pressure is exerted by the resilient material in some areas and significant force is lacking in others. Many attempts have been made to accomplish this personalized low back support as pressure on the spinal disks is optimized when sitting with the spine essentially straight. It is well known that the greatest pressure is exerted in the anterior sitting posture followed by the anterior straight and posterior sitting attitude, all of which are far greater than sitting with the back straight.

The need for an auxillary device that conforms exactly to the contour, form and configuration of the lumbar area of the back has long been needed, as chairs and seats of all kinds may not be conductive by themselves to purvey the optimum support in that area.

Further, attempts to use inflatable devices have normally been limited to removable cushions, or those built directly into the chair or seat, which again are not personalized nor continually conform when the user changes position in the seat.

With the foregoing in mind, it becomes a primary object of the invention to provide a device that is continually worn and pneumatically conforms to the exact shape and configuration of the users back. A belt holds the cushion in intimate and continual contact with the lower body and the resilient nature of the air chamber allows uniform pressure to be exerted directly into the lumbar curvature. Not only does the device consistantly support the affected section, but the amount of pressure may be regulated to the most comfortable level relieving the myositis of muscle stress or fatigue.

An important object of the invention further combines this pressure with heat which has been used successfully for muscle stress, strain, fatigue, and even spasms. The heating system is embedded into the surface of the air cushion and elevates the temperature of the device to a comfortable level even through the persons clothing and greatly adds to the therapeutic utility of the invention.

Another object allows the use of the device in a building where power for the heater is available, or in an automobile. The largest portion of time spent by an individual is in these locations. During times of limited activity, many people are especially effected by low back pain, such as relaxing in a chair or when driving in an automobile. Since the device is adapted to both alternating and direct current power, its use as a heater may be realized by connecting to the utility outlet of a building, or the cigarette lighter in an automobile. This eliminates storage batteries completely that have a short life and are limited in power. Batteries for heating have been attempted in some prior art, however, severe time and capacity limitations restrict their use. Since ample power is available in a structure, or an automobile, a switch is incorporated into the invention to control the desired heat intensity allowing optimal use with varying thickness of clothing.

Yet another object of the invention provides a comfortable, easy to wear brace, either under or outside of one's clothing. An adjustable buckle allows the device to be thus utilized as the length is sufficient in either circumstance.

A further object of the disclosure provides proper and paragon support for the spine, thus eliminating lumbar spine distortion. As well as maintaining the normal lordotic curve, vertical spine alignment is achieved as the normal lateral contour of the back horizontally includes convex sides which add support and are secured optimally by the belt in any seated or standing position.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 5 is an isometric view of an embodiment utilizing an electrical pump as the means to inflate the air chamber.

FIG. 6 is a cross-sectional view taken along lines 6—6 of FIG. 5.

FIG. 7 is an electrical schematic illustrating the heater circuitry in the preferred embodiment.

BEST MODE FOR CARRYING OUT THE INVENTION

The best mode for carrying out the invention is presented in terms of a preferred, second and third embodiments. All three embodiments are primarily designed alike, except the means to inflate the air chamber differ.

The preferred embodiment, as shown in FIGS. 1 through 4 and 7 is comprised of a belt 20 with one end having a buckle 22 attached permanently. The other end of the belt is retained by the buckle 22 allowing the belt to be attached around; one's waist and removed in a conventional manner. This belt 20 may be of any material suitable for the application, including woven synthetic fiber, leather, reinforced silicone rubber, or composite thermoplastics. Integral with the belt 20 is an air chamber 24 that is located on the surface opposite the buckle 22 that is in contact with the wearers lumbar region of the lower back. The chamber 24 is wider than the belt 20 and is configured to support the area of one's back between the sacrum and the dorsal portions almost the full width. The sides taper to a narrower width thus allow comfort and mobility to the user. The chamber 24 is air tight and separated forming a front and a back with the peripheral side walls expandable to yield a conformable resilient barrier.

A heater 26 is integrally embedded within the air chamber 24 on the inside surface next to the wearer. This heater 26 consists of metallic resistance wires or an etched metallic foil with nickel chromium as the resistance metal, either solid or in a stranded form. The heater 26 converts the electrical energy passing therethrough into heat as electrical resistance is encountered. This heat is directly dissipated into the wearers body providing physiologic relief of low back pain.

Figure 1:
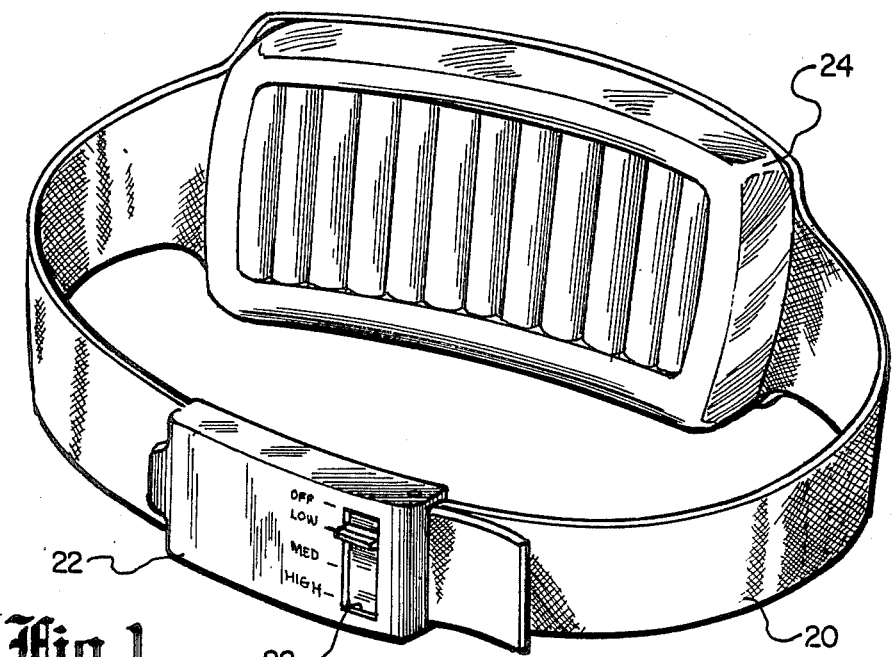
FIG. 1 is a partial isometric view of the preferred embodiment.

The resistance wires of the heater 26 are separated into a number of circuits allowing a step control of the intensity of the heat conducted from the brace to the wearers body. This may be accomplished by a wide variety of methods, such as shown in FIG. 7, which consists of three separate circuits with the first or "low" heat passing current through the entire length of resistance with the "medium" and "high" circuit correspondingly shorter lengths providing a greater resistance in each circumstance. It will be noted, however, that this electrical scheme is only one of a myriad of possibilities that will function equally well in the invention. In any event, the capacity is controlled by a manual switch 28 having electrically conducting contact points for directing the flow of electricity to the selected circuits for the desired capacity modulation. The switch 28 may be housed as an integral part of the buckle 22, as shown in FIG. 1, or may be in a separate enclosure attached to the belt 20, as illustrated in FIG. 5. Either embodiment of the mounting method may be used with equal ease.

Figure 4:
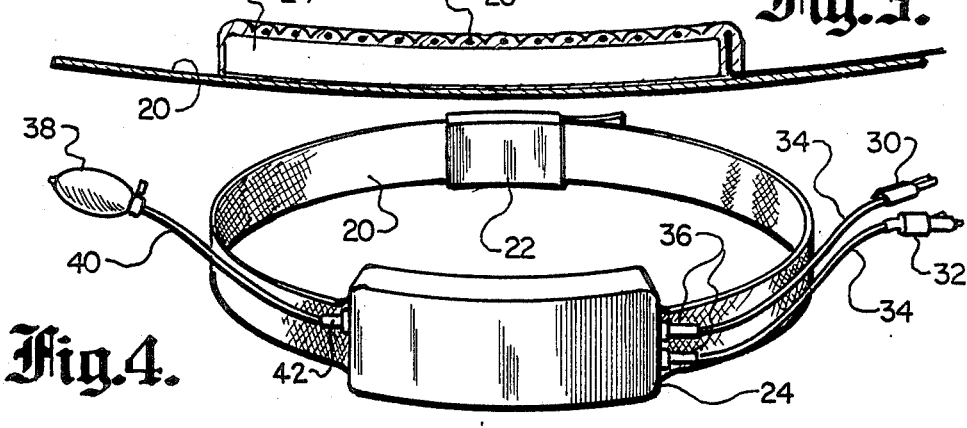
FIG. 4 is an isometric view of the preferred embodiment illustrating the manual bulb as the means to inflate the air chamber.

The flexibility of the system incorporates a dual alternating current and direct current power source. The alternating current, such as 120 volt single phase 60 Hertz, commonly found in homes and buildings, and 12 volt direct current, found in most automobiles, is utilized. This utility provides a power source easily obtainable to the person wearing the inflatable device. FIG. 7 illustrates the preferred electrical system which incorporates a 2 or 3 prong plug 30 for the A.C. power and a cigarette lighter adapter 32 for the D.C. input. A flexible cord 34 is used for both systems to connect to the belt 20 consisting of a pair of insulated stranded copper electrical conductors. In order to facilitate easy use of longer or shorter wires and to make the brace adaptable to be worn not connected to an electrical power source, a two conductor quick disconnect plug and socket 36 is provided. Although this element is not necessary for function of the invention, its use offers further flexibility. The socket 36 is attached permanently to the belt 20 in a convenient location, preferably as shown in FIG. 4, and the plug 36 to the end of the cord 34. Both the A.C. and D.C. are duplicated allowing separate and independent circuits. In either case, the power is interrupted by the switch 28. This may be any type suitable for the application, such as a slide, toggle, or rotary switch, each having the single pole, four position capabilities. The interconnection of the wiring from the switch 28 to the heater 26 may be on the surface or embedded within the belt 20 itself.

In order to provide the necessary biomechanical restriction to the specific muscles in the lumbar region and provide an even and a self-contouring surface, the air chamber 24 is inflated to the desired degree of firmness.

There are three separate embodiments that comprise the means to inflate this chamber 24. The preferred embodiment, illustrated in FIG. 4, incorporates a hand actuated bulb 38 that includes a manual valve and is attached to the air chamber 24 through a hose 40. A self-sealing quick disconnect 42 is attached to the belt structure 20. In operation, the bulb 38 is squeezed by hand, increasing the pneumatic pressure within the chamber. This action utilizes manual force, causing the bulb 38 to become smaller in mass driving the volume of air into the chamber 24. The disconnect 42 allows the bulb 38 and hose 40 to be removed after the inflation procedure is completed. For deflation, or an adjustment reducing the pressure the hose 40 is simply connected and the integral bulb valve opened.

Figures 2, 3:
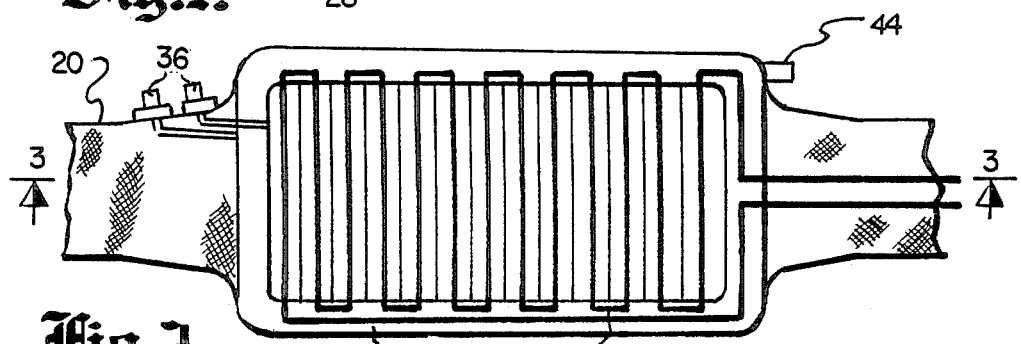
FIG. 2 is a partial view of the preferred embodiment as viewed from the inside.
FIG. 3 is a cross-sectional view taken along lines 3—3 of FIG. 2.

The second embodiment is illustrated pictorially in FIG. 2 and consists of a valve 44 located in an outermost portion of the air chamber 24. The valve 44 is opened and the chamber 24 is inflated orally by blowing up the interior with ones mouth. When sufficient pressure is applied, the valve is closed either by rotation, reversing, or positioning a plug according to the type of valve utilized. Another variation of this embodiment allows the chamber 24 to be inflated by a ordinary hand pump well known in the art, or compressed air, with the valve 44 having a SCHRATER mechanism therein such as used in automobile or bicycle tires.

The third embodiment is shown in FIGS. 5 and 6 and consists of an electrical pump 46 that contains valves capable of both increasing the pressure and maintaining the desired firmness of the device. The pump 46 preferably contains a bellows along with the requisite valves and allows automatic inflation with either an A.C. or D.C. power source.

In use, the belt 20 is inflated and fastened around the waist with the buckle 22. When the inclination for heat is perceived, the plug 30 or adapter 32 is connected to the appropriate power source and the switch 28 is positioned to the desired heat intensity. The tightness around the waist is adjusted by the buckle 22 and the firmness of the chamber 24 is controlled by the air pressure.

While the invention has been described in complete detail and pictorially shown in the accompanying drawings, it is not to be limited to such details, since many changes and modifications may be in the invention without departing from the spirit and the scope thereof. For example, although the chamber 24 is usually placed around the lumbar area, it can also be moved to the front to support and provide soothing heat to the muscles in the stomach region. Hence, it is described to cover any and all modifications and forms which may come within the language and scope of the appended claims.

I claim:

1. A heated lumbar positioned air inflatable physiotherapeutic brace comprising:
    (a) a belt completely encircling one's waist in a conformal manner with said belt having ends therewith; and a buckle attached permanently to one end of said belt receiving and removably captivating the other end,
    (b) an air chamber integral with said belt on the surface contiguously engaging a persons lumbar area creating resilient yielding homogeneous pressure,
    (c) a heater integrally embedded within said air chamber providing an elevated temperature within the brace providing physiologic relief of muscle myositis in the form of stress, strain, or fatigue, said heater further comprises metallic resistance wires embedded into the structure of the air chamber that is in physical contact with one's lumbosacral region, the wires having a resistance such that when an electrical current is passed therethrough that the energy is transformed into heat directly dissipated to the wearer's body, said resistance wires are separated into a plurality of circuits allowing a step control of the intensity of the heat conducted from the brace to one's body, said resistance wires further comprise an alternating current electrical power source and a direct current power source duplicating said resistance wires in such a manner as to provide heating when connected to either source independent of the other, said heater further having control means in the form of a manual switch having contact points for conducting electricity through circuits of said heater providing steps control of resistance for capacity modulation, and,
    (d) means to inflate said air chamber to a pressure of sufficient intensity to provide a biomechanical restriction to specific muscles in the lumbar region for the ambulatory management of low back pain, said means to inflate further comprise a hand actuated bulb, having a manual valve, associateably joined to said air chamber and self-sealing disconnect means functioning such that said chamber is inflated by the squeezing of one's hand on the bulb increasing pneumatic pressure within the chamber using manual force which causes the bulb to become smaller in volume, driving air into the chamber and removal of the bulb without the loss of pressure characterized by the self-sealing function of the quick disconnect means.

* * * * *